United States Patent [19]

Arieh et al.

[11] 4,418,577

[45] Dec. 6, 1983

[54] PROCESS FOR MEASURING AND ANALYZING POTENTIALS OF PIEZO-ELECTRIC ORIGIN GENERATED BY A RIGID MEMBER MADE OF AN ORGANIC MATERIAL

[75] Inventors: Simon Arieh; Guy Courvoisier; Jean-Louis Prost, all of Geneva, Switzerland

[73] Assignee: Battelle Memorial Institute, Carouge, Switzerland

[21] Appl. No.: 400,667

[22] Filed: Jul. 22, 1982

Related U.S. Application Data

[63] Continuation of Ser. No. 198,005, Nov. 3, 1980, abandoned.

[30] Foreign Application Priority Data

Feb. 5, 1979 [CH] Switzerland ............... 1085/79

[51] Int. Cl.³ .............................................. G01B 7/16
[52] U.S. Cl. ................................. 73/772; 73/DIG. 4; 128/774; 280/DIG. 13
[58] Field of Search .............. 73/DIG. 4, 772, 862.68, 73/862.04, 794; 128/774, 782; 364/508; 280/611, DIG. 13

[56] References Cited

U.S. PATENT DOCUMENTS 3,640,130  2/1972  Spescha et al. ................ 73/862.04
4,033,183  7/1977  List et al. ...................... 73/862.04 X
4,235,243  11/1980  Saha ............................. 128/774 X

OTHER PUBLICATIONS

Bazhenov–"Piezoelectric Properties of Wood", Consultants Bureau, N.Y., 1961, pp. 23–24.
Lakes et al.–"Device for Determining Bone Properties", Medical Instrumentation–vol. 12, No. 2, 1978, pp. 106–109.
Saha et al.–"Non-Invasive Techniques Using the Piezoelectric Effect", IEEE Transactions–vol. BMF-24, No. 6, Nov. 1977, pp. 508–512.

*Primary Examiner*—Charles A. Ruehl
*Attorney, Agent, or Firm*—Karl F. Ross; Herbert Dubno

[57] ABSTRACT

This process involves detecting piezo-electric potentials which are characteristic of a mechanical strain exerted on a long rigid member made of organic material. For this purpose, the potentials at two points spaced apart on this member are measured by means of two operational amplifiers $CI_1$ and $CI_2$ in order to obtain a signal which is characteristic of the stress rather than of its derivative and these signals are processed by means of analog operators $OA_1$, $OA_2$, $OA_3$ in order to identify the bending $\Delta F$ and torsional T stresses which are then compared with reference values RT, RF in order, for example, to trigger a signal. This process can be used for opening a safety ski binding.

12 Claims, 3 Drawing Figures

4,418,577

PROCESS FOR MEASURING AND ANALYZING POTENTIALS OF PIEZO-ELECTRIC ORIGIN GENERATED BY A RIGID MEMBER MADE OF AN ORGANIC MATERIAL

CROSS REFERENCE TO RELATED APPLICATIONS

The present application is a continuation of Ser. No. 198,005 filed Nov. 3, 1980, now abandoned, as a national phase application of PCT application No. PCT/CH80/00016 filed Feb. 4, 1980 and claiming the priority of Swiss application No. 1085/79 filed Feb. 5, 1979 under the International Convention. This application also includes subject matter from disclosed documents.

FIELD OF THE INVENTION

The invention relates to a process for measuring and analyzing potentials of piezo-electric origin generated in a long rigid member of an organic material as the result of a mechanical strain applied to this member.

BACKGROUND OF THE INVENTION

Scientific work has demonstrated that different organic substances produce variations in electric potentials as they are deformed. This is the case, in particular, with muscles.

It has already been proposed that signals of muscular origin be used to control the automatic opening of a ski binding if the skier is in danger of breaking his leg. A safety device of this type forms the subject of German Pat. No. 2 121 827, and U.S. pat. Nos. 3,776,566 and 3,826,509.

However, this solution poses more problems than it solves. In fact, although any muscular activity generates a variation in electric potential, these Patents remain silent with regard to the manner of deliberately using these currents to generate a control signal for opening the fastener. Skiing is inevitably accompanied by muscular work. Now the fastener must only be opened under exceptional circumstances at the moment when the strains on the bones of the leg become abnormal.

It is consequently necessary to define a threshold from which a signal resulting from the electric potential of muscular origin is to be generated. The definition of this threshold poses extremely complex problems since the strains to which the leg is subjected and those which are exerted on the muscles are not necessarily proportional nor simultaneous.

Moreover, electric potentials of muscular origin do not permit determination of the type of stress to which the bones are subjected. The resistance of a bone is not the same if it is subjected to bending or to torsion. This means that the electric potentials of muscular origin can, in certain cases, exceed the critical threshold while the strain on the bone is perfectly tolerable whereas, in other cases, this critical threshold is not attained when the bone is subjected to a stress exceeding its critical value.

The deficiencies and dangers of the earlier systems appear immediately and seem to be inherent in the very design of this safety device since it measures electric potentials dependent on muscular activity and these potentials are considered to be characteristic of the strains exerted on the bones.

Scientific work has also demonstrated that piezo-electric effects are exhibited when rigid members made of organic materials such as wood or bone are subjected to mechanical strains. Tests have shown that the forms of signal generated by the electric potentials as a result of the strains exerted on the bones differ depending on the nature of the stress and that the amplitude of the signal is dependent both on the size of the stress and the rate of application thereof. This means that, for a given stress level, the signal measured will depend on the speed of application of the stress.

OBJECTS OF THE INVENTION

In view of the foregoing, it is an object of the invention to measure the type and amplitude of the stresses exerted on a bone or on a wooden rod in order to compare the result with a typical stress. Another object of the invention is to provide a method using this comparison for different purposes, in particular, to release a ski fastener when the stress recorded on the skier's leg exceeds a permissible limit or for other purposes which will be enumerated below.

SUMMARY OF THE INVENTION

To this end, the present invention provides a process for measuring and analyzing potentials of piezo-electric origin generated by a long rigid member made of an organic material as a result of a mechanical pull on this member. This process is characterized by the fact that signals which are characteristic of the potentials are detected at two longitudinally spaced points which are at least adjacent to the surface of this member, in that each of these signals is amplified and integrated, in that the types of stresses generating the said signals are identified and these stresses are measured separately. More specifically a method of determining stresses in an elongated rigid member of organic material resulting from mechanical action upon said member which is substantially fixed at one end, comprises the steps of:

detecting piezoelectric potentials at two points along the member spaced apart by a predetermined distance and spaced from the fixed or captured end and forming the potentials into respective signals $S_1$, $S_2$;

amplifying and integrating the signals generated at each of the two points:

determining a difference $S_1 - S_2 = F^1$ between the values of the amplified and integrated signals;

multiplying the difference $F^1$ by the ratio $\Delta = D/d$ of the distance D between said end and the said point most distal therefrom and the distance d between the points to obtain a value F of flexion stress $F = \Delta F^1$; and detecting the difference between the greater $S_1$ of the signals and the value of said flexion stress to obtain a value $T = S_1 - \Delta F^1$ of torsional stress.

BRIEF DESCRIPTION OF THE DRAWING

The attached drawing illustrates schematically and by way of example a method of carrying out the process forming the subject of the invention. In the drawing.

SPECIFIC DESCRIPTION

If the detection of piezo-electric potentials originating from bones is intended to release a ski fastener, for example once a predetermined stress threshold has been attained, it is necessary to measure independently the two components from which the signal is formed in order to discover the distribution between torsional stresses and bending stresses.

It is well-known from strength of materials theory that the stress is constant at all the points on a beam fixed at one end in the event of torsion whereas the stress increases towards the fixing point in the event of bending.

Figure 2:
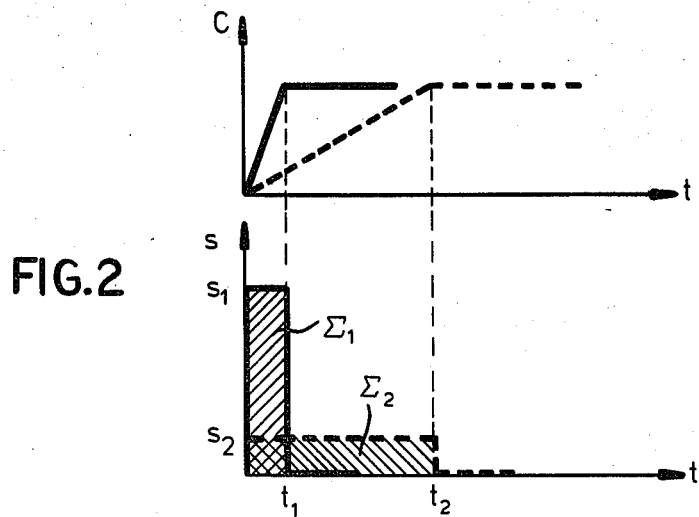
FIGS. 2 and 3 are explanatory graphs.

Moreover, it is also known that the voltage of piezoelectric origin is dependent on the rate of application of the stress. As shown in the graph in FIG. 2, the application of a stress C for a period $t_1$ gives a signal $s_1$ over the same period $t_1$ whereas the application of the same stress T over a period $t_2$ gives a signal $s_2$ of smaller amplitude over the same period $t_2$.

On the other hand, the surfaces $\epsilon_1$ and $\epsilon_2$ are equal. Consequently, by integrating the signal S, the notion of the "time" parameter is introduced and this integration brings us back to the stress itself rather than its derivative.

Figure 1:
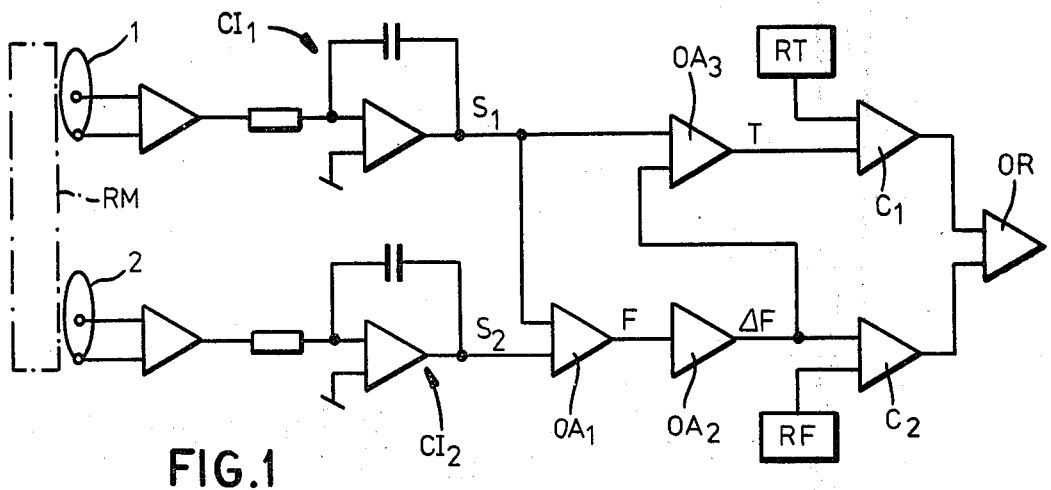
FIG. 1 is an electronic diagram for the processing of the signals picked up.
Figure 3:
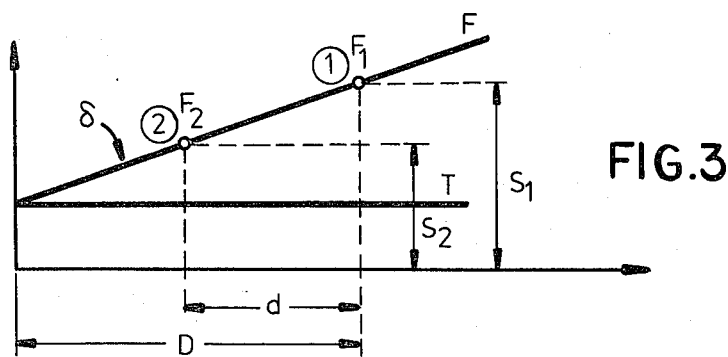

This result can be obtained by means of two active integrating circuits with operational amplifiers illustrated in FIG. 1 which essentially comprises two test electrodes 1 and 2 located at two longitudinally spaced points which are at least adjacent to the surface of a long rigid member RM made of an organic material. Each of these electrodes is connected to an active integrating circuit with an operational amplifier $Cl_1$ and $Cl_2$, at the output of which there appear the signals $S_1$ and $S_2$ respectively which are characteristic of the potentials and the time measured. These signals are then processed by a series of analog operators arranged so as to effect the mathematical processes to be explained with reference to the graph in FIG. 3.

This graph shows a straight line $\delta$ which corresponds to the sum of two torsional T and bending F stresses respectively of a fixed beam, and the lower portion of the leg, in particular the tibia, can be compared to this case.

The signals $S_1$ and $S_2$ which are measured at two points 1 and 2 on this straight line $\delta$ and are spaced by a distance d, $S_1$ being at a distance D from the fixing point, correspond to the sum of both the torsional and bending stresses at these points on the straight line $\delta$.

$$S_1 = T + F_1$$

$$S_2 = T + F_2$$

$$S_1 - S_2 = F_1 - F_2 = F^1$$

The straight line has an equation of the following type:
y=ax+b
a is the inclination of $\delta = F/d$
b is the ordinate at the origin = T at point 1 on the straight line $\delta$.

$$S_1 = \frac{F^1}{d} D + T$$

or again $S_1 = \frac{D}{d} F^1 + T$

In this equation, T is the unknown $$T = S_1 - \frac{D}{d} F^1 = S_1 - \Delta F$$

-continued
$$F = \frac{D}{d} F^1 = \Delta F.$$

In order to solve this equation from the signals $S_1$ and $S_2$ resulting from the active integrating circuits $Cl_1$ and $Cl_2$, an analog operator $OA_1$ with its two inputs connected to the outputs $Cl_1$ and $Cl_2$ establishes the difference between these signals $S_1$ and $S_2$ so that the value F appears at the output of this operator $OA_1$. A second analog operator $OA_2$ multiplies this value F by $\Delta$ which corresponds to D/d.

The value $\Delta F$ issuing from the operator $OA_2$ is directed, on the one hand, towards an input of an analog operator $OA_3$ whose second input is connected to the output of the integrator $Cl_1$. This operator $OA_3$ establishes the difference between $S_1$ and $\Delta F$ so that the value T appears at its output.

Two comparators $C_1$ and $C_2$ compare the values of T and $\Delta F$ respectively with a reference value RT and RF corresponding, for example, to the permissible torsional and bending limit respectively in the case of a safety ski binding. These two comparators which emit a signal as soon as one of these limits is exceeded are connected to an "OR" gate designed to deliver the useful signal controlling the release of the fastener.

Of course, the quality and precision of the measurements taken by means of the process described above depend essentially on the cleanness of the picked up signal being amplified. This cleanness can be influenced by various factors, in particular by potentials not originating from the bone but, for example, from the muscular activity inevitably accompanying the stresses applied to the bone, in particular during skiing.

Some tests were carried out both in the laboratory and on the leg of skiers moving about on the ski slopes in order to measure these potentials in vivo. These tests were firstly carried out using a pair of single electrodes. Although the potentials recorded by these electrodes permitted the variations to be measured as a function of the stresses applied to the bone, the graphs recorded by means of a recorder of the type used for electro-cardiograms showed a significant proportion of parasitic potentials, making it difficult to process a signal resulting from this electrode since, for certain stresses, the amplitude of the signal originating from the variations in potential generated by the piezo-electric effect due to the bone can be of the same order of magnitude as the parasitic potentials.

Some tests were then carried out using a pair of double electrodes, the test electrode being surrounded by a guard collar. A conducting cream of the type used for recording electro-cardiograms was used in order to improve the contact between the electrode and the skin. The electrodes were placed along the tibia which is directly adjacent to the skin over a large proportion of its length.

The cleanness of the signal recorded under these conditions is significantly better than in the previous case and permits the signal to be processed by the process described above.

Of course, the process forming the subject of the invention is not restricted to use for producing a signal for releasing a ski fastener. This application is only given as an example. In fact, other applications can be considered, for example medical applications in order to detect a fracture or a fissure or the state of healing of a fracture. Applications in the sphere of sport, particularly in sports training can also be considered. In fact, it is conceivable to detect the stresses on the tibia of a jumping or running athlete. The tibia is not the only bone on which the potentials of piezo-electric origin can be measured, the bones of the forearm also being close to the skin, making it possible to measure the stresses resulting from the playing of tennis and, consequently, to record the faults in a player's technique. This process is obviously not limited to the bones, but can be applied to other rigid members made of organic material such as wood, permitting measurement of the state of the stresses being exerted on wooden structures.

We claim:

1. A process for measuring and analyzing potentials of piezo-electric origin generated by a long rigid member made of an organic material as the result of a mechanical strain on this member, characterized by the fact that the signals which are characteristic of the potentials are detected at two longitudinally spaced points at least adjacent to the surface of this member, in that each of these signals is amplified and integrated, that the types of stresses generating the said signals are identified and that these stresses are measured separately.

2. A process according to claim 1, characterized by the fact that, in order to identify these stresses, the difference between the two integrated signals is established, the result being a characteristic of a bending stress, the bending stress of this characteristic is deduced and the value of the bending stress is subtracted from the greater of the integrated signals in order to obtain the torsional stress.

3. A process according to claim 2, characterized by the fact that a control signal is generated each time that at least one of the values measured exceeds the reference value.

4. A process according to claim 1, characterized by the fact that each of the stresses measured is compared with a reference value.

5. A method of determining stresses in an elongated rigid member of organic material resulting from mechanical action upon said member which is substantially fixed at one end, said method comprising the steps of:
 detecting piezoelectric potentials at two points along said member spaced apart by a predetermined distance and spaced from said end and forming said potentials into respective signals;
 amplifying and integrating the signals generated at each of said points;
 determining a difference between the values of the amplified and integrated signals;
 multiplying said difference by the ratio of the distance between said end and the said point most distal therefrom and the distance between said points to obtain a value of flexion stress; and
 detecting the difference between the greater of said signals and said vaue of said flexion stress to obtain a value of torsional stress.

6. The method defined in claim 5, further comprising the step of comparing respective signals representing each of said stresses with a respective reference value.

7. The method defined in claim 6, further comprising the step of generating a command signal upon a signal representing at least one said stresses exceeding the respective reference value.

8. The method defined in claim 7, wherein said points are spaced apart points along a skier's tibia, said method further comprising releasing a ski binding engaging said tibia in response to said command signal.

9. The use of the method defined in claim 5 for the opening of a ski binding upon one of said stresses exceeding a predetermined threshold value.

10. An apparatus for determining stresses in an elongated rigid member of organic material resulting from mechanical action upon said member which is substantially fixed at one end, and responds as a beam fixed at one end, said apparatus comprising:
 means for detecting piezoelectic potentials at two points along said member spaced apart by a predetermined distance and spaced from said end and forming said potentials into respective signals;
 means for applying and integrating the signals generated at each of said points;
 means for determining a difference between the values of the amplified and integrated signals;
 means for multiplying said difference by the ratio of the distance between said end and the said point most distal therefrom and the distance between said points to obtain a value of flexion stress; and
 means for detecting the difference between the greater of said signals and said value of said flexion stress to obtain a valve of torsional stress.

11. The apparatus defined in claim 9 wherein said means for detecting includes respective electrodes positioned at said points, said means for amplifying and integrating includes respective integrating circuits connected to said electrodes, and said means for determining and multiplying includes a first operational amplifier connected to said integrating circuits for generating a signal representing the difference between the signals from said integrating circuits, a second operational amplifier for multiplying the output of said first operational amplifier by a value representing said ratio to produce an output of said second operational amplifier representing flexion stress, a third operational amplifier being connected to the integrating circuit of the electrode at the point most distal from said end and to said second operational amplifier for producing an outputs at said third operational amplifier representing torsional stress, said third operational amplifier constituting said means for detecting the difference.

12. The apparatus defined in claim 11, further comprising respective comparators connected to the outputs of said second and third operational amplifiers for comparing the respective output signals with reference signals representing threshold values of flexural and torsional stress.

* * * * *